United States Patent [19]

Arrighi et al.

[11] Patent Number: 5,378,365
[45] Date of Patent: Jan. 3, 1995

[54] PROCESS FOR THE ISOLATION OF HIGHLY PURIFIED FACTORS IX, X AND II FROM PROTHROMBIN COMPLEX OR HUMAN PLASMA

[75] Inventors: Silvana Arrighi, Casciano di Murlo; Francesco Norelli; Maria G. Borri, both of Siena; Enzo Bucci, Cittaducale, all of Italy

[73] Assignees: Sclavo S.p.A., Siena; Aima-Derivati S.p.A., Prov. of Lucca, both of Italy

[21] Appl. No.: 38,942

[22] Filed: Mar. 26, 1993

[30] Foreign Application Priority Data

Mar. 27, 1992 [IT] Italy .......................... FI92 A 000078

[51] Int. Cl.$^6$ .............................................. B01D 15/08
[52] U.S. Cl. .................................... 210/635; 210/656; 530/384; 530/413; 530/416
[58] Field of Search ............ 210/635, 656, 659, 198.2; 530/384, 413, 416

[56] References Cited

U.S. PATENT DOCUMENTS

| 4,395,396 | 7/1983 | Eibl ..................... 530/384 |
| 4,470,968 | 9/1984 | Mitra ................... 530/384 |
| 4,720,385 | 1/1988 | Lembach ............... 530/384 |
| 4,981,952 | 1/1991 | Yan ..................... 530/384 |
| 5,061,789 | 10/1991 | Moller ................. 530/384 |
| 5,138,034 | 8/1992 | Uemura ................ 530/384 |
| 5,286,849 | 2/1994 | Herring ................ 530/384 |

FOREIGN PATENT DOCUMENTS

| 52827 | 6/1982 | European Pat. Off. ............ 530/384 |
| 239565 | 9/1987 | European Pat. Off. ............ 530/384 |

OTHER PUBLICATIONS

H. Suomela et al, "Preparation and properties of a Therapeutic Factor IX Concentrate", *Vox Sang.*, 33: 37–50, (1977).

M. Wickerhauser, et al, "Development of Large-Scale Fractionation Methods", *Vox Sang.*, 22: 137–160, (1972).

J. Heystek, et al, "Contributions to the Optimal Use of Human Blood", *Vox Sang.*, 25: 113–123, (1973).

J. Tharakan, et al, "Development of an Immunoaffinity Process for Factor IX Purification", *Vox Sang.*, 58: 21–29, (1990).

C. Michalski, et al, "Large-Scale Production and Properties of a Solvent-Detergent-Treated Factor IX Concentrate from Human Plasma", *Vox Sang.*, 55: 202–210, (1988).

T. Burnouf, et al, "Properties of a Highly Purified Human Plasma Factor IX:c Therapeutic Concentrate Prepared by Conventional Chromatography," *Vox Sang.*, 57: 225–232, (1989).

J. P. Miletich, et al, "Purification of Human Coagulation Factors II, IX and X Using Sulfated Dextran Beads", *Meth. Enzymol.*, 80: 221–228, (1981).

Bessos, et al, "Immunopurification of Human Coagulation Factor IX Using Monoclonal Antibodies", *Thromb. Haemostasis*, 56(1) 86–89, (1986).

K. Smith, "Immunoaffinity Purification of Factor IX from Commercial Concentrates and Infusion Studies in Animals", *Blood*, 72: 1269–1277, (1988).

*Primary Examiner*—Ernest G. Therkorn
*Attorney, Agent, or Firm*—Stevens, Davis, Miller & Mosher

[57] ABSTRACT

A description is given of a process for the purification of factor IX, factor X, and factor II from human plasma or fractions thereof, wherein a solution containing prothrombin complex factors is purified by repeated ion exchange chromatographic separations followed by adsorption chromatography on metal ions.

6 Claims, No Drawings

PROCESS FOR THE ISOLATION OF HIGHLY PURIFIED FACTORS IX, X AND II FROM PROTHROMBIN COMPLEX OR HUMAN PLASMA

FIELD OF THE INVENTION

The present invention refers to a process for the purification of factor IX, factor X, and factor II from human plasma or fractions thereof containing same by repeated anion exchange chromatographic separations followed by chromatography on selective adsorption resin. The process gives highly purified products.

STATE OF THE ART

A fundamental approach to the treatment of congenital disorders of coagulation factors consists in the replacement therapy, i.e. the intravenous administration of the deficient factor. The said therapeutic approach requires that coagulation factors concentrates containing high-activity deficient factor be readily available in injectable small volumes. The ever increasing importance of said therapy made it topical to develop processes giving the aforesaid products of improved quality and purity.

The conventional processes utilized so far [Wickerhauser N., Sgouris J. T.: "Development of large scale fractionation methods. II. Isolation of a factor IX concentrate (prothrombin complex) for clinical use", Vox Sang., 22, 137–160 (1972); Heystek J., Brummelhuis H. G. J., Krijnen R. W.: "Contribution to the optimal use of human blood. II. The large scale preparation of prothrombin complex. A comparison between two methods using the anion exchangers DEAE-cellulose DE-52 and DEAE-Sephadex A-50", Vox Sang., 25, 113–123 (1973); Suomela H., Myllyla G., Raaska E.: "Preparation and properties of a therapeutic factor IX concentrate", Vox Sang., 33, 37–50 (1977); Miletich J. P., Broze G. J., Majerus P. W.: "Purification of human coagulation factors II, IX, and X using sulfated dextran beads", Meth. Enzymol., 80, 221–228 (1981)] are essentially based on chromatographic methods giving concentrates of different purity, consisting of various vitamin-K dependent proteins: factor II (prothrombin), factor VII (proconvertin), factor IX (Christmas factor), factor X (Stewart-Prower factor), known as prothrombin complex factors. Actually, the aforesaid concentrates are commonly used to treat factors II, IX, and X deficiencies.

Within the hemophilic syndrome range (hemophilia A or factor VIII deficiency, hemophilia B or factor IX deficiency, hemophilia C or factor XI deficiency), hemophilia B is the second most important as for the number of cases and-like hemophilia A-one of the most serious due to the frequent occurrence of hemorrages.

The prolonged administration of prothrombin complex concentrates to patients suffering from hemophilia B may cause hypercoagulability and disseminated intravascular coagulation (DIVC), probably caused by factors II and X overload and/or by the presence of trace amounts of activated factors, such as IXa, Xa, and IIa. The need was therefore felt to produce pure concentrates of the single factors. Out of the innovative processes developed so far, some are based on immunoaffinity chromatography [Bessos H., Prowse C. V.: "Immunopurification of human coagulation factor IX using monoclonal antibodies", Thromb. Haemostasis, 56, 86 (1986); Smith K.: "Immunoaffinity purification of factor IX from commercial concentrates and infusion studies in animals", Blood, 72, 1269 (1988); Tharakan J., Strickland D., Burgess W., Drohan W. N., Clark D. B.: "Development of an immunoaffinity process for factor IX purification", Vox Sang., 58, 21–29 (1990)]. The said processes give a high-specific-activity product, which, however, may be contaminated by viruses and heterologous proteins. It follows that the product obtained by the aforesaid processes must be further purified and controlled, before use, to check the presence of contaminants, if any.

Therefore, processes giving products of high specific activity and high purity, without being adversely affected by the aforesaid inconveniences, were developed [Michalski C., Bal F., Burnouf T., Goudemand M.: "Large-scale production end properties of a solvent-detergent-treated factor IX concentrate from human plasma", Vox Sang., 55, 202–210 (1988); Burnouf T., Michalski C., Goudemand M., Huart J. J.: "Properties of a highly purl lied human plasma factor IX:C therapeutic concentrate prepared by conventional chromatography", Vox Sang., 57, 225–232 (1989)].

The abovesaid methods use anion exchangers, the final step being affinity chromatography based on a stationary phase functionalized by sulphated compounds, such as heparin.

DETAILED DESCRIPTION OF THE INVENTION

The process as per the present invention gives a highly purified factor IX (specific activity higher than 100 I.U./mg protein) free from the other factors of the prothrombin complex (PTC) and isolates highly purified factor II and factor X by two successive ion exchange chromatographic separations (at saline and pH conditions allowing the removal of most of contaminating proteins and in particular of some PTC components) followed by adsorption chromatography on a metal ions (in particular copper ions) derivatized matrix.

Purification as per the present invention is carried out by PTC batchwise adsorption from plasma and/or the fractions thereof on an anion exchange resin (e.g. DEAE-Sephadex A-50) and use of phosphate buffers: TL1 (0.02M dibasic sodium phosphate, 0.02M monobasic potassium phosphate, 0.16M sodium chloride) at pH 6.9±0.1 for resin washing; TE1 (0.1M dibasic sodium phosphate, 0.1M monobasic potassium phosphate, 0.8M sodium chloride) and TE2 (0.05M dibasic sodium phosphate, 0.05M monobasic potassium phosphate, 0.4M sodium chloride) at pH 6.9±0.1, for elution of the aforesaid proteins. The PTC solution, after three-step elution by DEAE-Sephadex, suitably stabilized, diluted, and filtered, is subjected to viral inactivation by chemical agents, e.g. 0.3% TNBP and 1% Tween 80, maintained in contact under stirring at 24° C. for 6 h min. The PTC inactivated solution, after control and, if necessary, restoration of the suitable saline concentrations, is cooled to 0°–5° C., filtered and applied to a column containing DEAE-Sepharose Fast Flow, conditioned with phosphate/citrate buffer (5 mM sodium citrate, 2.5 mM dibasic sodium phosphate, 2.5 mM monobasic potassium phosphate) containing 0.19M sodium chloride (TL2) at pH ranging from 6 to 6.5. The operation utilizes a flow rate of 45–65 cm/h and a batch of 20–40 I.U. factor IX per ml resin.

The surfactants used to inactivate viruses and most of unbound proteins are removed in the flow through and by resin washing with approx. one column volume of TL2.

Weakly bound proteins and approx. 70% factor X are eluted by washing the resin with 18 column volumes min. of phosphate/citrate buffer containing 0.26M sodium chloride (TL3) at pH 6.1±0.1.

Factor X is recovered with purity Of approx. 20 I.U./mg protein. The product containing factor IX is then eluted with 5 column volumes min. of phosphate/citrate buffer consisting of 0.28-0.36M (preferably 0.29M) sodium chloride (TE4) at pH 6.1±0.1.

The solution obtained, which contains factor IX with a specific activity generally ranging between 5 and 15 I.U./mg proteins, is adequately stabilized, ultrafiltered against buffer TD1 (20-100 mM—preferably 50 mM—sodium acetate, 0.2-1M—preferably 0.5M—sodium chloride) at pH 7.2±0.2, filtered, and then applied to a column containing copper ions supported on sepharose gel, conditioned with buffer TD1. The operation utilizes a flow rate of 20-60 cm/h and a batch of 30-100 I.U. factor IX per ml gel.

The column is first washed with one volume of TD1 to remove contaminating unbound proteins and then with 8-10 volumes of buffer TL4 (buffer TD1 containing 40-80 mM—preferably 60 mM—glycine) at pH 7.2±0.2 to elute the more weakly bound proteins, and in particular factors II and X. Factor IX is then eluted with buffer TE5 (50 mM sodium acetate, 500 mM sodium chloride, 0.08-0.12M—preferably 0.1M—glycine) at pH 7.2±0.2.

The eluates containing the respective factors are stabilized, diafiltered, concentrated, filtered, and freeze-dried.

The further advantages and characteristics of the present invention will be apparent from the following example, which is illustrative only; in no event is it to be regarded as limiting the scope of the claimed invention.

EXAMPLE

Step 1

Frozen fresh human plasma (1000 l approx.) was thawed at 0°-5° C. under continuous stirring and dry-centrifuged. The precipitate, a cryopaste, was collected. It may be used, e.g., for factor VIII purification.

The supernatant plasma was cooled to 0°-1° C.; the pH was adjusted to 6.9 with 1M acetate buffer. PTC factors were adsorbed on an anion exchange resin, i.e. DEAE-Sephadex A-50 (previously expanded in TL1 and sterilized), added to the plasma at a ratio of 1.5 g dry resin/l plasma, and maintained in contact, under stirring at 1°-3° C. for 45 min. approx. After the aforesaid contact time, the resin was allowed to settle for some hours. Then, after decanting the supernatant plasma, which was recovered and further fractionated to obtain antithrombin III, gammaglobulins, albumin, etc. concentrates, the suspension left, which consisted of plasma residue+resin+PTC, was collected. Plasma residue and unbound proteins were removed by washing the resin with a TL1 buffer volume approximating ⅔ of the plasma initial volume, at 4° C.

The PTC factors (i.e. factor IX, factor X, factor II, and trace amount of factor VII) adsorbed on the resin, were first eluted with a buffer TE1 volume approximating 1/10 of the plasma initial volume, then twice with TE2, each time with a TE2 volume approximating 1/10 of the plasma initial volume.

The eluted PTC solution (50-60% recovery and 1-2 I.U. factor IX/mg protein specific activity) was collected in a suitable container and stabilized by heparin addition at a concentration of 0.75 units/ml solution. Osmolarity being restored by diafiltration or dilution with $H_2O$ added with stabilizer, the solution was filtered under sterile conditions.

Step 2

The solution obtained in step 1 was added, by conventional techniques, with a mixture of surfactants, in particular TNBP at 0.3% concentration and Tween 80 at 1% concentration, and maintained in contact under mild stirring at 24° C. for 6 hours.

Step 3

The inactivated PTC solution was controlled, the pH was adjusted to 6.1±1 and the physiological saline conditions were restored. Then the solution was cooled to approx. 4° C., filtered through clarifying membranes and applied to a column containing approx. 15-20 l DEAE-Sepharose Fast Flow (previously conditioned with TL2 at pH 6.1±0.1) at a flow rate of approx, 55 cm/h. Non-adsorbed proteins were removed by washing out the resin with one column volume of TL2; weakly bound proteins and most factor X were removed by column washing with 18 volumes of TL3.

Factor IX, part of factor II and of factor X were eluted with 5 column volumes of TE4. The recovery was of 60-70% and the specific activity of approx. 10 I.U. factor IX/mg protein. After concentration to 1/10 of the initial volume, the solution was diafiltered on 30,000 d cut-off membranes against 2.5-4 vol. TD1.

Step 4

The adequately concentrated PTC solution was filtered through clarifying membranes and applied to a column filled with Chelating Sepharose derivatized with copper ions, previously conditioned in TD1. The operation utilizes a flow rate of 30 cm/h and a batch of 50 I.U. factor IX per ml resin.

Non-adsorbed proteins were removed by washing out with one column volume of TD1. Factor II and factor X residue were eluted with TL4: more precisely, factor II was collected in the second, third, and fourth column washing beds, and factor X residue was collected in the sixth, seventh, and eighth washing beds. Factor IX was eluted with TE5 and approx. 4 column beds were collected. Recovery was of approx. 75% of the I.U. applied.

The eluate containing factor IX with specific activity approximating 100 I.U./mg protein was concentrated to 50 I.U. ml, diafiltered against 5 volumes on a 30,000 d cut-off ultrafilter to restore physiological conditions, suitably stabilized by addition of 0.03 I.U. antithrombin III per I.U. factor IX, filtered under sterile conditions, poured into vials, and freeze-dried.

Factor II and factor X recovery was 60% of the applied amount; the specific activity of factor II approximated 30 I.U./mg proteins and that of factor X 20 I.U./mg proteins. Eluates were concentrated to 50 I.U./ml, diafiltered, suitably stabilized, filtered under sterile conditions, and freeze-dried.

We claim:

1. Process for the purification of factor IX, factor II and factor X from human plasma by two successive ion exchange chromatographic separations followed by adsorption chromatography on a metal ions derivatized matrix.

2. The process according to claim 1 wherein the adsorption chromatography matrix is derivatized with copper ions.

3. The process according to claim 2 wherein:
a) the supernatant plasma, after cryopaste centrifugation and removal, is purified by adsorption of anion exchange resin and the adsorbed product is further eluted,
b) the product collected in (a) is subjected to vital inactivation and filtered, and the obtained solution is applied again to an anion exchange column,
c) the product obtained after elution in (b) is concentrated and diafiltered, and the solution obtained is caused to flow through a column derivatized with copper ions, the adsorbed products are eventually eluted: factor II is collected in the second, third, and fourth washing beds, factor X in the sixth, seventh, and eighth washing beds, finally factor IX is collected.

4. The process according to claim 3 wherein purification on anion exchange resin is conducted by eluting the product to be collected first with a buffer consisting of 0.1M dibasic sodium phosphate, 0.1M monobasic potassium phosphate, 0.8M sodium chloride, at pH 6.9±0.1 and then with a buffer consisting of 0.05M dibasic sodium phosphate, 0.05M monobasic potassium phosphate, 0.4M sodium chloride at pH 6.9±0.1.

5. The process according to claim 3 wherein the operation as per point b) utilizes an anion resin flowed through by the solution to be purified at a rate of 55 cm/h; non-adsorbed or weakly adsorbed proteins (among which factor X) are washed, respectively, with a buffer consisting of 5 mM sodium citrate, 2.5 mM dibasic sodium phosphate, 2.5 mM monobasic potassium phosphate containing 0.19M sodium chloride at pH ranging from 6 to 6.5, and with a buffer consisting of 5 mM sodium citrate, 2.5 mM dibasic sodium phosphate, 2.5 mM monobasic potassium phosphate containing 0.26M sodium chloride at pH 6.1±0.1, then the adsorbed product (among which factor IX) is eluted with a phosphate/citrate buffer containing 0.28-0.36M sodium chloride at pH 6.1±0.1.

6. The process according to claim 3 wherein the operation as per point c) utilizes a copper ions derivatized column, conditioned with 20-200 mM sodium acetate, 0.2-1M sodium chloride at pH 7.2±0.2, unbound proteins are removed by washing with the aforesaid buffer, then factor II is collected by elution with 20-100 mM sodium acetate, 0.2-1M sodium chloride, 40-80 mM glycine, at pH 7.2±0.2 in the second, third, and fourth washing beds, factor X is collected with the same buffer in the sixth, seventh, and eighth washing beds, and factor X by elution with 50 mM sodium acetate, 500 mM sodium chloride, and 0.08-0.12M glycine, at pH 7.2±0.2.

* * * * *